United States Patent [19]

Paggini et al.

[11] 4,358,625
[45] Nov. 9, 1982

[54] METHOD FOR THE PRODUCTION OF HIGH-PURITY ETHYLENE GLYCOLS

[75] Inventors: Alberto Paggini, Spino D'Adda; Ugo Romano, Milan; Donato Furlone, Novate Milanese; Domenico Sanfilippo, Milan, all of Italy

[73] Assignee: Snamprogetti, S.p.A., Milan, Italy

[21] Appl. No.: 19,109

[22] Filed: Mar. 9, 1979

Related U.S. Application Data

[63] Continuation of Ser. No. 851,296, Nov. 14, 1977, abandoned.

[30] Foreign Application Priority Data

Nov. 17, 1976 [IT] Italy ................................. 29386 A/76

[51] Int. Cl.³ ............................................. C07C 31/20
[52] U.S. Cl. .................................................... 568/867
[58] Field of Search .......................................... 568/867

[56] References Cited

U.S. PATENT DOCUMENTS

| 2,867,651 | 1/1959 | Wise | 568/913 |
| 3,597,452 | 8/1971 | Laemmle et al. | 568/860 |
| 3,860,520 | 1/1975 | Lindemuth et al. | 568/913 |
| 3,904,656 | 9/1975 | Broz | 568/867 |
| 3,970,711 | 7/1976 | Reiche et al. | 568/867 |

FOREIGN PATENT DOCUMENTS

| 1025852 | 3/1958 | Fed. Rep. of Germany . |
| 32559 | 11/1964 | German Democratic Rep. . |
| 912797 | 12/1962 | United Kingdom . |

OTHER PUBLICATIONS

Taylor, "Chem. Abstracts", vol. 56, (1962), 2590d.

*Primary Examiner*—Joseph E. Evans
*Attorney, Agent, or Firm*—Morgan, Finnegan, Pine, Foley & Lee

[57] ABSTRACT

A method is disclosed for obtaining high-purity ethylene glycols in which the improvement consists in reducing the oxygen-containing organic impurities by treating their aqueous solutions as obtained during the processing of ethylene oxide with a solution of an alkali metal borohydride, sodium borohydride being preferred.

A definitely alkaline environment is preferred. Ethylene glycols can thus be obtained which are particularly suitable for use in the fibre-manufacturing industry. Such glycols have extremely low UV-absorbance values.

4 Claims, No Drawings

METHOD FOR THE PRODUCTION OF HIGH-PURITY ETHYLENE GLYCOLS

This is a continuation of application Ser. No. 851,296, filed Nov. 14, 1977, now abandoned.

This invention relates to a method for the production of high-purity ethylene glycols.

According to the conventional art, ethylene glycols are produced commercially according to a two-stage method. The first stage comprises the step of producing ethylene oxide, and during this stage, the catalytic oxidation of ethylene is carried out in the presence of air or of oxygen. The second stage consists in the hydration of the ethylene oxide, as prepared in the previous stage, to ethylene glycol.

As a result of the oxidation of ethylene there are produced, in addition to ethylene oxide, carbon dioxide and water, also small amounts of impurities which contain oxygen, such as $CH_3CHO$, $HCHO$ together with other aldehydes and oxygen-containing compounds. These compounds, along with other compounds as formed in the purification and recovery stages, can be found, distributed among the several liquid or gaseous streams of the recovery and purification cycle until they are finally found both in the as-produced ethylene oxide and in the liquors present in the installation.

The liquors present in the installation contain, in addition to such by-products, also a not negligible amount of monoethylene glycol.

In the subsequent stage, that is that of glycol-production, the ethylene oxide is admixed with water, at appropriate concentrations and pH values, and is then treated at a temperature of about 100° C.–200° C., the hydration of ethylene glycol to the glycols being thus achieved. The as-produced glycols are then separated from the water in excess and subjected to purification steps and to the final rectification run.

Considerable advantages could be achieved, would it be possible to use for the hydration of ethylene oxide the same watery liquors as produced in the ethylene oxide producing stage.

Such waters, if and when utilized, should not be treated in the purification installation prior to being dumped, the water consumption of processing water would be smaller or even annulled for the hydration reaction and, at least, it would be possible to recover the glycol as contained in the waters coming from the first stage, so that the final yield would be increased by as much as from 2% to 5%.

These facts would be conducive to a considerable improvement in the production of glycols.

The oxygen-containing impurities, no matter if deriving from the waters of ethylene oxide portion or contained in the oxide itself are composed not only by the aldehydes indicated hereinabove but also by compounds having high Ultra Violet extinction coefficients and go to pollute the finished monoethylene glycol which shows high-absorbance values of Ultra Violet radiations. Such high values do not fulfil the most stringent specifications for the use in the fibre-manufacturing industry.

According to the conventional art, many authors suggest for such process expensive and intricate approaches such as for example the use of activated charcoal or of exchange resins which considerably affect the purification cycle.

These suggestions have not been industrially tested hitherto and in the present-day installations which are run for the production of high-purity glycols, the waters of the ethylene-oxide-production stage are dumped from the cycle, whereas, for the hydration of ethylene oxide water is fed at a high purity rating, such as demineralized water, for the necessary water topping up.

The present invention permits that there may be employed, for the hydration of ethylene oxide, the same waters produced in the preparation of ethylene oxide, without thereby incurring the shortcomings enumerated hereinabove.

The present invention contemplates the step of adding borohydrides of alkali metals to the glycol waters of the installation. Such addition can be carried out both before and/or after the admixture of such waters with ethylene oxide. The borohydrides of alkali metals can be used both in the form of solids or in that of stabilized solutions.

At present, the borohydride which is the most attractive from an economical standpoint is sodium borohydride, $NaBH_4$.

Sodium borohydride in aqueous solution, however, tends to become decomposed into $H_2$ and $NaBO_2$, such phenomenon being fostered by a temperature increase and hindered by high pH values. At present, $NaBH_4$ is stored either in the solid powdered state or as an aqueous solution stabilized with caustic soda, the weight ratio of soda to borohydride being about 3 times. A typical commercial composition is the following:

| | |
|---|---|
| $NaBH_4$ | 12% by weight |
| NaOH | 38% by weight |
| $H_2O$ | 50% by weight |

The following TABLE reports the decomposition velocity of $NaBH_4$ from its solutions.

| SOLUTION | | | Temp. | | |
|---|---|---|---|---|---|
| $NaBH_4$ | NaOH | $H_2O$ | °C. | pH | Decomposition in time |
| 0.4 | 3.8 | balance | 24 | 14 | about 1% after 24 hrs |
| 0.4 | 3.8 | balance | 47 | 14 | about 16% after 24 hrs |
| 12 | 38 | balance | 25 | 14 | about 0% after 24 hrs |
| 0.009 | 0.029 | balance | 150 | 11.5 | 100% after 45 seconds approx. |
| 0.017 | 0.055 | balance | 150 | 11.8 | 100% after 60 seconds approx. |
| 0.009 | 0.029 | balance | 80 | 11.5 | 100% after 2 hrs. approx. |

A surprising aspect of the invention is that the reduction of the oxygen-containing compounds takes place levels of a few parts per million (ppm) by employing nearly stoichiometrical amounts of $NaBH_4$ with respect to the compounds to be reduced, while operating at the same temperatures of the hydration step (40° C. to 200° C.) and under pH values even below 12. It is preferred that the amount of alkali metal borohydride employed be approximately 1–3 times the stoichiometric amount required for reducing the oxygen-containing compounds.

The glycol obtained by treating the glycolic waters of the installation with $NaBH_4$ shows low values of UV-absorbance and fulfils the most severe specifications as prescribed for the use in the fibre-producing industry.

In addition to the considerable advantages achieved when using the waters of the ethylene-oxide production stage for the hydration of same oxide to glycols as outlined above, the present invention permits other improvements in the overall technology of the glycol production.

The ethylene oxide to be forwarded to the production of the glycols does not require the final purification treatments, the result being savings in first and running costs. In addition to that, in the rectification under vacuum of the monoethylene glycol lower reflux ratios can be adopted.

Inasmuch as the commercial technology for the glycol production have several processing patterns, it is not possible to indicate beforehand the points which are preferred, in the installations, for reducing the present invention to constructive practice.

A skilled technician is capable, at any rate, to spot the procedures for working this invention, once he has, before him, the processing layout of any of the commercial technological processes for glycol production.

The concept of the present invention includes the method for removing oxygen-containing compounds contained in aqueous solutions by treating such solutions with alkali metal borohydrides at a pH of from 10 to 12.

A better understanding of the advantages and the procedures of the present invention can be achieved from the ensuing few Examples which are anyway not to be construed as limitations.

EXAMPLE 1

A glycol-producing industrial plant is fed with high-purity ethylene oxide (aldehyde value 20 ppm as acetaldehyde) as well as with watery liquors consisting for the 37% of recycled waters and for the 63% of demineralized water. Upon hydration and separation of the excess water, monoethylene glycol is separated and rectified under vacuum. Monoethylene glycol exhibits UV absorbance values of 0.04 at 220 millimicron and of 0.005 at 260 millimicron wavelength. The product fulfils the most stringent specifications for use in the production of fibres.

EXAMPLE 2

A glycol-producing commercial plant is fed with high-purity ethylene oxide (aldehyde contents 20 ppm as acetaldehyde) as well as with waters which are composed for their 37% by recycled waters and for their 63% by water coming from the ethylene oxide section. Upon hydration and separation of the excess waters, the mono-ethylene glycol is separated and rectified under vacuum. The monoethylene glycol displays an UV absorbance value of 0.20 at 220 millimicron and 0.40 at 260 millimicron. The yield of the monoethylene glycol over the ethylene which has been employed is increased by 3.3% with respect to EXAMPLE 1. The as-produced monoethylene glycol does not fulfil the most severe specification for fibre-making.

EXAMPLE 3

The same hydration product as obtained according to the procedure of EXAMPLE 2 is supplemented at 150° C. with a solution of sodium borohydride at a rate of 40 mls per cubic meter of effluent. The solution contains 12% by weight of $NaBH_4$ and 38% by weight of NaOH, the balance being water. After the operations of separation and purification, the values of Ultra Violet absorbance of the as-produced monoethylene glycol are 0.05 at 220 millimicron and 0.020 at 260 millimicron. This monoethylene glycol fulfils the most severe specifications for use in making fibres.

EXAMPLE 4

A glycol-producing commercial installation is fed with non-purified ethylene oxide (aldehyde contents, as acetaldehyde, definitely over 400 ppm) as well as with waters composed for 37% by recycled waters and for 63% by water coming from the ethylene oxide section. After hydration, separation of the excess waters and purification, the as-produced monoethylene glycol shows UV-absorbance values of 0.40 at 220 millimicron and of 0.60 at 260 millimicron. This product is unsuitable for fibre-making. The monoethylene glycol yield with respect to the ethylene used is increased by 4.2% with respect to EXAMPLE 1.

EXAMPLE 5

The reaction effluent of EXAMPLE 4 is supplemented by the solution of sodium borohydride of EXAMPLE 3, at a rate of 90 mls per cubic meter. The UV-absorbance values of the purified monoethylene glycol are 0.12 at 220 millimicron and 0.025 at 260 millimicron. This monoethylene glycol is fully suitable for fibre-making. The yield of monoethylene glycol with respect to the ethylene employed is increased by 4.2% over EXAMPLE1.

EXAMPLE 6

When operating with the charge reported for EXAMPLE 2 above, but supplementing the waters emerging from the ethylene oxide section with the sodium borohydride solution of EXAMPLE 3, at 60° C., at a rate of 40 mls per cubic meter, there are obtained about the same values of UV-absorbance as in EXAMPLE 1, with savings of 40% approximately of sodium borohydride as compared with EXAMPLE 3.

We claim:

1. A method for the production of ethylene glycol of high purity having low values of U.V. absorbance comprising hydration of ethylene oxide to ethylene glycol wherein the hydration of ethylene oxide is effected using water produced during the manufacture of ethylene oxide by the catalytic oxidation of ethylene, additional water sufficient to effect hydration of the ethylene oxide, and an alkali metal borohydride.

2. A method as claimed in claim 1 wherein said alkali metal borohydride is sodium borohydride.

3. A method as claimed in claim 1 wherein said hydration is carried out at a temperature of 40°–200° C. at an alkaline pH.

4. A method claimed in claim 1 wherein said alkali metal borohydride is employed in amounts of 1 to 3 times the stoichiometric amount required for reducing oxygen-containing compounds in said water.

* * * * *